United States Patent
Racha et al.

(10) Patent No.: US 11,260,369 B2
(45) Date of Patent: Mar. 1, 2022

(54) CATALYTIC COMPOSITION, METHOD OF MAKING AND CATALYTIC APPLICATION THEREOF FOR PRODUCING ESTER(S) OF GLYCEROL

(71) Applicant: BHARAT PETROLEUM CORPORATION LIMITED, Mumbai (IN)

(72) Inventors: Arundhathi Racha, Greater Noida (IN); Chiranjeevi Thota, Greater Noida (IN); Dharmendra Pandey, Greater Noida (IN); Dattatraya Tammanna Shastri Gokak, Greater Noida (IN); Sanjay Bhargava, Greater Noida (IN)

(73) Assignee: BHARAT PETROLEUM CORPORATION LIMITED, Mumbai (IN)

(*) Notice: Subject to any disclaimer, the term of this patent is extended or adjusted under 35 U.S.C. 154(b) by 167 days.

(21) Appl. No.: 14/959,014

(22) Filed: Dec. 4, 2015

(65) Prior Publication Data
US 2016/0158729 A1 Jun. 9, 2016

(30) Foreign Application Priority Data
Dec. 5, 2014 (IN) .................. 3917/MUM/2014

(51) Int. Cl.
| | |
|---|---|
| *B01J 21/06* | (2006.01) |
| *B01J 21/16* | (2006.01) |
| *B01J 23/10* | (2006.01) |
| *B01J 23/745* | (2006.01) |
| *B01J 37/02* | (2006.01) |
| *B01J 37/08* | (2006.01) |
| *C07C 67/08* | (2006.01) |
| *C10L 1/02* | (2006.01) |
| *C10L 10/14* | (2006.01) |
| *C10L 1/19* | (2006.01) |
| *C10L 10/10* | (2006.01) |

(52) U.S. Cl.
CPC ............ *B01J 21/16* (2013.01); *B01J 21/063* (2013.01); *B01J 23/10* (2013.01); *B01J 23/745* (2013.01); *B01J 37/0236* (2013.01); *B01J 37/08* (2013.01); *C07C 67/08* (2013.01); *C10L 1/026* (2013.01); *C10L 1/191* (2013.01); *C10L 10/10* (2013.01); *C10L 10/14* (2013.01)

(58) Field of Classification Search
CPC ........ C07C 31/225; C07C 67/08; B01J 21/16; B01J 21/063; B01J 23/10; B01J 23/745; B01J 37/0236; B01J 37/08; C10L 1/026
See application file for complete search history.

(56) References Cited

U.S. PATENT DOCUMENTS

| | | | | | |
|---|---|---|---|---|---|
| 6,083,473 | A | * | 7/2000 | Esquivel | ............. C01B 17/0465 |
| | | | | | 423/244.01 |
| 6,551,658 | B1 | * | 4/2003 | Clough | ..................... C23C 8/02 |
| | | | | | 427/212 |
| 2008/0216391 | A1 | * | 9/2008 | Cortright | ................. C10G 3/45 |
| | | | | | 44/307 |

FOREIGN PATENT DOCUMENTS

| | | | | |
|---|---|---|---|---|
| JP | 2014042865 A | * | 3/2014 | |
| WO | WO-2012122245 A1 | * | 9/2012 | ............ B01J 29/048 |

OTHER PUBLICATIONS

Tomonori Kawabata, Masaki Kato, Tomoo Mizugaki, Kohki Ebitani, and Kiyotomi Kaneda, Monomeric Metal Aqua Complexes in the Interlayer Space of Montmorillonites as Strong Lewis Acid Catalysts for Heterogeneous Carbon-Carbon Bond-Forming Reactions, 2005, Chem Eur J. 11, 288-297 (Year: 2005).*
Kohki Ebitani et al., Simple and clean synthesis of 9,9-bis[4-(2-hydroxyethoxy)phenyl]fluorene from the aromatic alkylation of phenoxyethanol with fluoren-9-one catalysed by titanium cation-exchanged mont morillonite , 2000, Green Chemistry, 157-160 (Year: 2000).*
Machine Translation of JP2014042865A (Year: 2014).*
Tomoo Mizugaki, Racha Arundhathi, Takato Mitsudome, Koichiro Jitsukawa, and Kiyotomi Kaneda, Highly Efficient and Selective Transformations of Glycerol Using Reusable Heterogeneous Catalysts, 2014, ACS Sustainable Chemistry & Engineering 2 (4), 574-578 (Year: 2014).*
Goncalves et al., "Acetylation of glycerol catalyzed by different solid acids", Catalysis Today, vol. 133-135 (2008), pp. 673-677.
Ferreira et al., "Acetylation of glycerol over heteropolyacids supported on activated carbon", Catalysis Communications, vol. 12 (2011), pp. 573-576.
Khayoon et al., "Acetylation of glycerol to biofuel additives over sulfated activated carbon catalyst", Bioresource Technology, vol. 102 (2011), pp. 9229-9235.
Balaraju et al., "Acetylation of glycerol to synthesize bioadditives over niobic acid supported tungstophosphoric acid catalysts", Fuel Processing Technology, vol. 91 (2010), pp. 249-253.
Melero et al., "Acidic Mesoporous Silica for the Acetylation of Glycerol: Synthesis of Bioadditives to Petrol Fuel", Energy & Fuels, (2007), vol. 21, pp. 1782-1791.
Freese et al., "Acylation of aromatic compounds on H-Beta zeolites", Catalysis Today, vol. 49 (1999), pp. 237-244.

(Continued)

*Primary Examiner* — Ellen M McAvoy
*Assistant Examiner* — Ming Cheung Po
(74) *Attorney, Agent, or Firm* — Hamre, Schumann, Mueller & Larson, P.C.

(57) ABSTRACT

In accordance with the present subject matter there is provided a process for producing mono-, di- and triesters of glycerol over a catalyst composition. The catalyst composition including a base catalyst and a support material based on phyllosilicates of montmorillonite structure and the process for preparing the catalyst composition is also described.

20 Claims, No Drawings

(56) References Cited

OTHER PUBLICATIONS

Silva et al., "Catalytic acetylation of glycerol with acetic anhydride", Catalysis Communications, vol. 11 (2010), pp. 1036-1039.
Dosuna-Rodriguez et al., "Glycerol acetylation on sulphated zirconia in mild conditions", Catalysis Today, vol. 167 (2011), pp. 56-63.
Ferreira et al., "Glycerol acetylation over dodecatungstophosphoric acid immobilized into a silica matrix as catalyst", Applied Catalysis B: Environmental, vol. 91 (2009), pp. 416-422.
Liao et al., "Producing triacetylglycerol with glycerol by two steps: Esterification and acetylation", Fuel Processing Technology, vol. 90 (2009), pp. 988-993.
Kuang et al., "Structure and reactivity of silica-supported 12-tungstophosphoric acid", Applied Catalysis A: General, vol. 250 (2003), pp. 221-229.
Reddy et al., "Synthesis of bio-additives: Acetylation of glycerol over zirconia-based solid acid catalysts", Catalysis Communications, vol. 11 (2010), pp. 1224-1228.
Len et al., "Continuous flow transformations of glycerol to valuable products: an overview", Len and Luque Sustainable Chemical Processes ,2014, 2:1, pp. 1-10.
Khayoon et al., "Acetylation of glycerol to biofuel additives over sulfated activated carbon catalyst", , vpBioresource Technology, vol. 102 (2011), pp. 9229-9235.
Jagadeeswaraiah et al., "Selective esterification of glycerol to bioadditives over heteropoly tungstate supported on Cs-containing zirconia catalysts", Applied Catalysis A: General, vol. 386 (2010), pp. 166-170.

\* cited by examiner

CATALYTIC COMPOSITION, METHOD OF MAKING AND CATALYTIC APPLICATION THEREOF FOR PRODUCING ESTER(S) OF GLYCEROL

TECHNICAL FIELD

The subject matter described herein in general relates to a catalyst composition including a base catalyst on a support material. The present disclosure also relates to a process for preparation of a catalyst composition. The present disclosure further relates to a process for producing ester(s) of glycerol or substituted glycerol's by catalytic acylation of glycerol or substituted glycerol's in the presence of catalyst composition.

BACKGROUND

Biodiesel is produced by the transesterification of vegetable oils with methanol over alkali-based catalysts, as shown in Scheme 1.

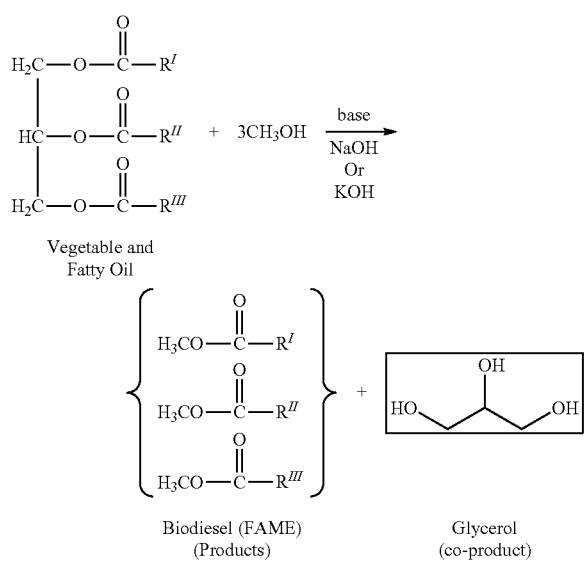

Scheme 1: Reaction Scheme for Biodiesel Production

About 10 wt % glycerol byproduct or co-product is generated during biodiesel synthesis. The increase of biodiesel production will result in the accumulation of glycerol. This not only creates a glut in the market but also affects the overall economics of biodiesel production. This situation has prompted a search for new applications of glycerol. Accordingly, glycerol can be a cost-effective raw material for the preparation of valuable chemicals and fuel additives. The utilization of glycerol to produce different value added chemicals has been studied (Len et al., Sustainable Chemical Processes, 2014, 2, 1).

Glycerol-based compounds, such as acetylglcyerols, are being widely used as fuel additives, intermediates in polymers, pharmaceuticals, cryogenics, and photographic materials. Monoacetyl glycerides (MAG), diacetyl glycerides (DAG), and triacetyl glycerides (TAG) are the main products (also known as mono-, di- and triacetin) obtained from the acetylation of glycerol in the presence of acetic acid and/or acetic anhydride (Liao et al., Fuel Process Technol., 2009, 90, 988-993; Ferreira et al., Catal. Commun, 2011, 12, 573-576). Among the obtained products, diacetin and triacetin are the most interesting products from a fuel-production point of view. They can be formulated with petroleum-derived fuels to improve either cold and viscosity properties (biodiesel) or antiknocking properties (gasoline). A large number of mono- and diacetyl glycerols are used as food preservatives.

There has been considerable research focused on the synthesis of acetylglycerols from crude glycerol using heterogeneous catalyst to make the biodiesel process economically viable. However, most of the acylation reactions are dominated by using acetic anhydride and non-aqueous condition. The conventional acylation reaction is poorly suited to the acylation of crude glycerol with acetic acid under aqueous conditions. The classic enzyme catalyzed reaction for the synthesis of acetylglycerols exhibits very good product selectivity from crude glycerol, however the process suffers from low yield, difficulty in product isolation, and economic viability.

Acylation of neat glycerol may be achieved by various heterogeneous catalysts. One such example of a heterogeneous catalyst is activated carbon (AC) that is obtained by treating the surface of the pre-catalyst with sulfuric acid at 85° C. for four hours to introduce acidic functionalities. The catalyst exhibits 91% glycerol conversion with a selectivity of 38%, 28% and 34% for mono-, di- and triacetyl glyceride, respectively (Hameed et al., Bioresource Technology, 2011, 102, 9229-9235).

Glycerol acetylation has been carried out using different heterogeneous acid catalysts such as Amberlyst-15, zirconia, niobic acid, HPAs and zeolites (Jagadeeswaraiah et al., Appl. Catal. A Gen, 2010, 386, 166-170; Silva et al., Catal. Commun, 2010, 11, 1036-1039; Balaraju et al., Fuel Process Technol., 2010, 91, 249-253; Ferreira et al., Catal. Commun, 2011, 12, 573-576). When Amberlyst-15 acid resin is used as a catalyst, a selectivity of 54% and 13% toward DAG and TAG, respectively can be achieved (Goncalves et al., Catal. Today, 2008, 133-135, 673-677). Comparatively, sulfated zirconia catalysts were considerably less active (Dosuna-Rodríguez et al., Catal. Today, 2011, 167, 56-63). In the presence of niobic acid-supported tungstophosphoric acid (TPA) catalyst, a relatively high selectivity of 57% and 20% toward the formation of DAG and TAG, respectively was recorded (Balaraju et al., Fuel Process Technol., 2010, 91, 249-253). By utilizing dodecatungstophosphoric acid immobilized into a silica matrix as a heterogeneous catalyst selectivity of 62% and 3% for DAG and TAG, respectively can be achieved (Ferreira et al., Appl. Catal. B Environ, 2009, 91, 416-422). However, some of these catalysts described above cannot be applied industrially. Some silicates are difficult to functionalize, heteropoly acids are soluble in polar media, zeolites have low surface area and thermal stability, and some materials are too expensive (Freese et al., Catal. Today, 1999, 49, 237-244; Kuang et al., Appl. Catal. A: General, 2003, 250, 221-229; Melero et al., Energy Fuels, 2007, 21, 1782-1791).

Despite the synthetic elegance and high turnover number, these processes suffer from serious limitations of using the neat glycerol which uses an expensive procedure for purification of crude glycerol that precluded the wide use in industry.

SUMMARY

The present disclosure relates to a catalyst composition comprising: a base catalyst selected from the group consisting of transitional metals, oxides of transitional metals, and combinations thereof in an amount in the range of 6 to 20% w/w of the total weight of the composition; and a support material in an amount in the range of 80 to 99% w/w of the total weight of the composition, wherein the support material is based on phyllosilicates of montmorillonite structure, with total surface area of 220 to 300 m²/g.

The present disclosure also relates to a process for producing a catalyst composition, the process comprising: contacting a salt of transitional metal with montmorillonite in a polar solvent to obtain a solution; ageing the solution at a temperature in the range of 25-80° C. for a time period in the range of 10 to 24 h; isolating a solid product; and drying the solid product at a temperature in the range of 50-150° C. for a time period in the range of 10 to 24 h to obtain a catalyst composition.

The present disclosure further relates to a process for producing ester of glycerol, the process comprising: contacting the catalyst composition with a compound of general Formula I

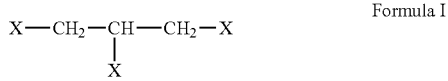

Formula I wherein 1-3 X groups are OH and 0-2 X groups are —OC(O)R1, wherein R1 is —(CH$_2$)$_n$—CH$_3$, wherein n is 0 to 30, wherein all R1 groups are identical or different in presence of HOC(O)R1, wherein R1 is —(CH$_2$)$_n$—CH$_3$, wherein n is 0 to 30 optionally in presence of a polar solvent at a temperature in the range of 100 to 180° C. for a period of 2 to 5 hours; and isolating glycerol esters, the glycerol esters having a general Formula II

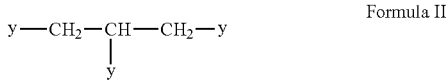

Formula II wherein 0-2 Y groups are OH and 1-3 Y groups are —OC(O)R1, wherein R1 is —(CH$_2$)$_n$—CH$_3$, wherein n is 0 to 30, wherein all R1 groups are identical or different.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter

DETAILED DESCRIPTION

The present invention now will be described more fully hereinafter. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to a catalyst composition which is used for acylation of glycerol or substituted glycerol's to produce ester(s) of glycerol or substituted glycerol's.

The catalyst composition of the present disclosure includes a base catalyst selected from the group consisting of transitional metals, oxides of transitional metals, and combinations thereof in an amount in the range of 6 to 20% w/w of the total weight of the composition; and a support material in an amount in the range of 80 to 99% w/w of the total weight of the composition, wherein the support material is based on phyllosilicates of montmorillonite structure, with total surface area of 220 to 300 m²/g.

In one implementation, the base catalyst is selected from the group consisting of scandium (Sc), titanium (Ti), iron (Fe), lanthanum (La), cerium (Ce), ytterbium (Yb), oxide of scandium (Sc), oxide of titanium (Ti), oxide of iron (Fe), oxide of lanthanum (La), oxide of cerium (Ce), oxide of Ytterbium (Yb), and combinations thereof. The metal in the catalyst composition may be present in their elemental form or as metal oxide or as metal salt or mixtures thereof. In another implementation, the base catalyst selected from the group consisting of scandium oxide (Sc$_2$O$_3$), titanium oxide (Ti$_2$O$_3$), iron oxide (Fe$_2$O$_3$), lanthanum trioxide (La$_2$O$_3$), cerium oxide (Ce$_2$O$_3$), ytterbium oxide (Yb$_2$O$_3$), and combinations thereof. In yet another implementation, the base catalyst may be present in the catalyst composition in cationic form. In one non-limiting example, the base catalyst is selected from the group consisting of lanthanum (La), oxide of lanthanum (La), and combinations thereof.

The base catalyst can be present in the catalyst composition in an amount in the range of 6 to 18% w/w of the total weight of the composition. In one implementation, the base catalyst is present in the composition in an amount in the range of 10 to 15% w/w of the total weight of the composition. In another implementation, 12% w/w base catalyst is present in the catalyst composition.

The present disclosure further relates to a catalyst composition, wherein the support material is selected from the group consisting of alumina, zirconia, titania, silica, niobia, zeolites, clay, mesoporous oxides and microporous oxides. In one non-limiting example, the support material is based on phyllosilicates of montmorillonite structure, with total surface area of 220 to 300 m²/g. Montmorillonite clay's are layered silicates and are among the numerous inorganic supports for reagents used in organic synthesis. They can be used as an efficient and versatile support as they have good cation exchange capacity, absorption capacity, bronsted and lewis acid sites, and the nature of swelling in polar solvents. In case of montmorillonite clay, both bronsted and lewis acidic catalytic sites are available hence its natural occurrence as well as ion exchange properties allow it to function efficiently as a catalyst. The interlayer cations are exchangeable, thus allowing alteration of the acidic nature of the material by simple ion-exchange procedure. Further, clays are safe to handle, reusable, inexpensive, can prevent waste, and promote atom economy. Clays may lower the activation energy of a reaction by stabilizing the transition state. In one implementation, the support material may be acid treated, preferably treated with a mineral or organic acid, more preferably with acetic acid.

The catalyst composition is used for preparation of mono-, di- and triesters of glycerol, and combinations thereof.

The present disclosure also relates to a process for producing a catalyst composition, the process comprising: contacting a salt of transitional metal with montmorillonite in a polar solvent to obtain a solution; ageing the solution at a temperature in the range of 25-80° C. for a time period in the range of 10 to 24 h; isolating a solid product; and drying the solid product at a temperature in the range of 50-150° C. for a time period in the range of 10 to 24 h to obtain a catalyst composition.

Salts of transitional metal can be simply any organic or inorganic transitional metal salts. In one implementation, salts of transitional metal include inorganic or organic salts of scandium (Sc), preferably selected from the group consisting of scandium (III) trifluromethanesulfonate ($C_4F_{12}O_{12}S_4Sc$), scandium (III) chloride hexahydrate ($ScCl_3.6H_2O$), scandium (III) hydroxide ($Sc(OH)_3$), scandium (III) nitrate hydrate ($Sc(NO_3)_3.xH_2O$), scandium (III) oxalate pentahydrate ($Sc_2(C_2O_4)_3.10H_2O$), scandium (III) sulfate pentahydrate ($Sc_2(SO_4)_3.5H_2O$). In one implementation, salts of transitional metal include inorganic or organic salts of titanium (Ti), preferably selected from the group consisting of titanium (IV) trifluromethanesulfonate ($C_4F_{12}O_{12}S_4Ti$), titanium (IV) chloride ($TiCl_4$), titanium (IV) nitrate ($Ti(NO_3)_4$), titanium (III) oxalate decahydrate ($Ti_2(C_2O_4)_3.10H_2O$), titanium (IV) sulfate ($Ti(SO_4)_2$). In one implementation, salts of transitional metal include inorganic or organic salts of iron (Fe), preferably selected from the group consisting of iron (III) trifluromethanesulfonate ($C_3F_9FeO_9S_3$), iron (III) chloride ($FeCl_3$), iron (III) hydroxide ($Fe(OH)_3$), iron (III) nitrate nonahydrate ($Fe(NO_3)_3.9H_2O$), iron (III) oxalate hexahydrate ($Fe(C_2O_4)_3.6H_2O$), iron (III) sulfate ($Fe_2(SO_4)_3$). In one implementation, salts of transitional metal include inorganic or organic salts of cerium (Ce), preferably selected from the group consisting of cerium (III) trifluromethanesulfonate ($C_3F_9Ce)_9S_3$), cerium (III) chloride heptahydrate ($CeCl_3.7H_2O$), cerium (III) hydroxide ($Ce(OH)_3$), cerium (III) nitrate hexahydrate ($Ce(NO_3)_3.6H_2O$), cerium (III) oxalate ($Ce_2(C_2O_4)_3$), cerium (III) sulfate octahydrate ($Ce_2(SO_4)_3.8H_2O$). In one implementation, salts of transitional metal include inorganic or organic salts of ytterbium (Yb), preferably selected from the group consisting of ytterbium (III) trifluromethanesulfonate ($C_4F_{12}O_{12}S_4Yb$), ytterbium (III) chloride hexahydrate ($YbCl_3.6H_2O$), ytterbium (III) hydroxide ($Yb(OH)_3$), ytterbium (III) nitrate pentahydrate ($Yb(NO_3)_3.5H_2O$), ytterbium (III) sulfate ($Yb_2(SO_4)_3$), and combinations thereof. In another implementation, salt of lanthanum metal is selected from the group consisting of lanthanum (III) trifluoromethanesulfonate ($C_3F_9S_3O_9La$), lanthanum (III) chloride heptahydrate ($LaCl_3.7H_2O$), lanthanum (III) hydroxide ($La(OH)_3$), lanthanum (III) nitrate hexahydrate ($La(NO_3)_3.6H_2O$), lanthanum (III) oxalate hydrate ($La_2(C_2O_4)_3.xH_2O$), lanthanum (III) sulfate nonahydrate ($La_2(SO_4)_3.9H_2O$), and combinations thereof. One non-limiting example of salt of lanthanum is lanthanum (III) trifluoromethanesulfonate. One non-limiting example of salt of scandium is scandium (III) trifluromethanesulfonate. One non-limiting example of salt of titanium is titanium (IV) trifluromethanesulfonate. One non-limiting example of salt of iron is ferric (III) chloride. One non-limiting example of salt of cerium is cerium (IV) trifluromethanesulfonate. One non-limiting example of salt of ytterbium is ytterbium (III) trifluromethanesulfonate.

The support material used in the present disclosure is selected from the group consisting of alumina, zirconia, titania, silica, niobia, zeolites, clay, mesoporous oxides and microporous oxides, preferably selected from phyllosilicates of montmorillonite structure, with total surface area of 220 to 300 m²/g. In one implementation the support material is acid treated, preferably with inorganic or organic acid, more preferably with acetic acid.

The present disclosure further relates to a process of preparing the catalyst composition, wherein polar solvent is selected from the group consisting of aromatic or aliphatic ethers, alcohols, amines, esters halogenated hydrocarbons, carboxylic acids, water, and combinations thereof. In another implementation, the polar solvent is selected from the group consisting of water, lower alcohol (C1-10), and combinations thereof. In one non-limiting example, the polar solvent can be water. Water used for the preparation of catalyst composition is distilled and deionized. Any other purified form of water preferably non-ionic can also be used.

In one implementation, process for producing a catalyst composition includes: contacting a salt of lanthanum with montmorillonite in water to obtain a solution; ageing the solution at 65° C. for 12 h; isolating a solid product; and drying the solid product at a temperature in the range of 110° C. for a time period in the range of 12 to 16 h to obtain a catalyst composition.

The present invention relates to an improved process for the preparation of acetylglcyerols. The present invention particularly relates to a process for preparation of acetylglcyerols from crude glycerol and acetic acid at mild or reduced temperatures. The present disclosure further relates to a process for producing ester of glycerol, the process comprising: contacting the catalyst composition comprising: a base catalyst selected from the group consisting of transitional metals, oxides of transitional metals, and combinations thereof in an amount in the range of 6 to 20% w/w of the total weight of the composition; and a support material in an amount in the range of 80 to 99% w/w of the total weight of the composition, wherein the support material is based on phyllosilicates of montmorillonite structure, with total surface area of 220 to 300 m²/g with a compound of general Formula I

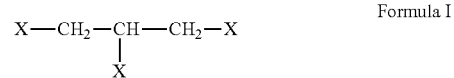

Formula I wherein 1-3 X groups are OH and 0-2 X groups are —OC(O)R1, wherein R1 is —$(CH_2)_n$—$CH_3$, wherein n is 0 to 30, wherein all R1 groups are identical or different in presence of HOC(O)R1, wherein R1 is —$(CH_2)_n$—$CH_3$, wherein n is 0 to 30 optionally in presence of a polar solvent at a temperature in the range of 100 to 180° C. for a period of 2 to 5 hours; and isolating glycerol esters, the glycerol esters having a general Formula II

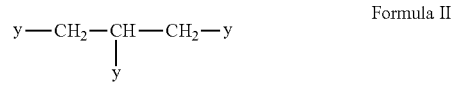

Formula II wherein 0-2 Y groups are OH and 1-3 Y groups are —OC(O)R1, wherein R1 is —$(CH_2)_n$—$CH_3$, wherein n is 0 to 30, wherein all R1 groups are identical or different.

In one implementation, the process for producing ester of glycerol includes the step of contacting the catalyst composition comprising: a base catalyst selected from the group consisting of transitional metals, oxides of transitional metals, and combinations thereof in an amount in the range of 6 to 20% w/w of the total weight of the composition; and a support material in an amount in the range of 80 to 99% w/w of the total weight of the composition, wherein the support material is based on phyllosilicates of montmorillonite structure, with total surface area of 220 to 300 m²/g with a compound of general Formula I

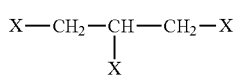
Formula I wherein 3 X groups are OH, in presence of HOC(O)R1, wherein R1 is —(CH$_2$)$_n$—CH$_3$, wherein n is 0 to 30 optionally in presence of a polar solvent at a temperature in the range of 100 to 180° C. for a period of 2 to 5 hours; and isolating glycerol esters, the glycerol esters having a general Formula II

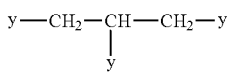
Formula II wherein 0-2 Y groups are OH and 1-3 Y groups are —OC(O)R1, wherein R1 is —(CH$_2$)$_n$—CH$_3$, wherein n is 0 to 30.

In another implementation, the process for producing ester of glycerol includes the step of: contacting the catalyst composition including a base catalyst selected from the group consisting of transitional metals, oxides of transitional metals, and combinations thereof in an amount in the range of 6 to 20% w/w of the total weight of the composition; and a support material in an amount in the range of 80 to 99% w/w of the total weight of the composition, wherein the support material is based on phyllosilicates of montmorillonite structure, with total surface area of 220 to 300 m²/g with a compound of general Formula I

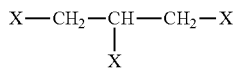
Formula I wherein 2 X groups are OH and 1 X groups are —OC(O)R1, wherein R1 is —(CH$_2$)$_n$—CH$_3$, wherein n is 0 to 30, in presence of HOC(O)R1, wherein R1 is —(CH$_2$)$_n$—CH$_3$, wherein n is 0 to 30 optionally in presence of a polar solvent at a temperature in the range of 100 to 180° C. for a period of 2 to 5 hours; and isolating glycerol esters, the glycerol esters having a general Formula II

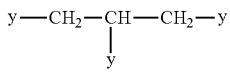
Formula II wherein 0-1 Y groups are OH and 2-3 Y groups are —OC(O)R1, wherein R1 is —(CH$_2$)$_n$—CH$_3$, wherein n is 0 to 30, wherein all R1 groups are identical or different.

In yet another implementation, the process for producing ester of glycerol includes: contacting the catalyst composition comprising: a base catalyst selected from the group consisting of transitional metals, oxides of transitional metals, and combinations thereof in an amount in the range of 6 to 20% w/w of the total weight of the composition; and a support material in an amount in the range of 80 to 99% w/w of the total weight of the composition, wherein the support material is based on phyllosilicates of montmorillonite structure, with total surface area of 220 to 300 m²/g with a compound of general Formula I

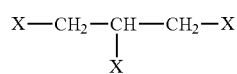
Formula I wherein 1 X group is OH and 2 X groups are —OC(O)R1, wherein R1 is —(CH$_2$)$_n$—CH$_3$, wherein n is 0 to 30, wherein all R1 groups are identical or different in presence of HOC(O)R1, wherein R1 is —(CH$_2$)$_n$—CH$_3$, wherein n is 0 to 30 optionally in presence of a polar solvent at a temperature in the range of 100 to 180° C. for a period of 2 to 5 hours; and isolating glycerol esters, the glycerol esters having a general Formula II

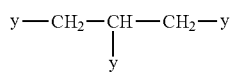
Formula II wherein 3 Y groups are —OC(O)R1, wherein R1 is —(CH$_2$)$_n$—CH$_3$, wherein n is 0 to 30, wherein all R1 groups are identical or different.

In one implementation, the compound of general Formula I has 1 X substituent as OH and 2 X substituent are —OC(O)R1, wherein R1 is —(CH$_2$)$_n$—CH$_3$, wherein n is 0-20, preferably 0-10, more preferably 0.

In one implementation, R1 of HOC(O)R1 is —(CH$_2$)$_n$—CH$_3$, wherein n is 0-20, preferably 0-10, more preferably 0.

In yet another implementation, R1 of general Formula II is —(CH$_2$)$_n$—CH$_3$, wherein n is 0-20, preferably 0-10, more preferably 0.

In one implementation, the process for producing ester of glycerol includes the step of contacting the catalyst composition comprising: a base catalyst selected from the group consisting of transitional metals, oxides of transitional metals, and combinations thereof in an amount in the range of 6 to 20% w/w of the total weight of the composition; and a support material in an amount in the range of 80 to 99% w/w of the total weight of the composition, wherein the support material is based on phyllosilicates of montmorillonite structure, with total surface area of 220 to 300 m²/g with a compound of general Formula I

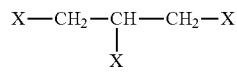
Formula I wherein 3 X groups are OH, in presence of HOC(O)R1, wherein R1 is —(CH$_2$)$_n$—CH$_3$, wherein n is 0 optionally in presence of water at a temperature in the range of 100 to 180° C. for a period of 2 to 5 hours; and isolating glycerol esters, the glycerol esters having a general Formula II

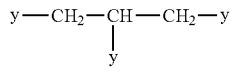
Formula II wherein 0-2 Y groups are OH and 1-3 Y groups are —OC(O)R1, wherein R1 is —(CH$_2$)$_n$—CH$_3$, wherein n is 0.

In one implementation, the concentration of HOC(O)R1 is 1-6 molar equivalent with respect to the compound of general Formula I.

In another implementation, the compound of general Formula I has a purity in the range of 70 to 99.9%

As described above, around 10 wt % glycerol byproduct or co-product is generated during biodiesel synthesis. The present disclosure relates to a process for the preparation of glycerolacetylo compounds that start with inexpensive crude glycerol and catalyzed by the catalyst composition preferably having lanthanum source and commercially available acetic acid at reduced temperature and time to yield MAG, DAG, and higher quantity of TAG. The process is economical and industrially feasible as it employs crude glycerol, acetic acid, low reaction temperature, easy recovery of the catalyst, and low cost of crude glycerol and acetic acid when compared with neat glycerol and acetic anhydride. The present disclosure more particularly relates to the development of efficient and recyclable catalyst system composing lanthanum oxide/montmorillonite for the acylation of crude glycerol using water as a solvent at ambient conditions.

Acylation of glycerol generally proceeds via an acyl-oxygen cleavage bimolecular (AAC2) mechanism: It can be expected that the rate of esterification could be affected due to the transient complexation of the metal ion with the carbonyl group.

Without being bound by theory, the density of the Bronsted acid sites in the acid-treated montmorillonite, i.e La-montmorillonite was treated with acetic acid to montmorillonite is increased over natural montmorillonite because the increased number of broken edges resulting from the broken layers favour the formation of esters assumed to proceed via the AAC2 mechanistic pathway. The presence of metal ion in the montmorillonite not only enhances the Lewis acidity but also Bronsted acidity which is generated from the interstitial cation-aqua complex of the metal ion. As described the intercalation of the metal-aqua complex formed in the montmorillonite with water present/formed during the reaction enables the generation of hydronium ion (Bronsted acidity) and metal hydroxide as described in the reversible reaction. The formation of the right admix ($[La^{3+}(OH)(H_2O)_{n-1}]^{2+}+H_3O^+$) of Bronsted and Lewis acid sites is able to facilitate the esterification reaction as described in the reversible reaction.

The consumption of Bronsted acid further shifts towards the right side to generate more of Bronsted acidity. Water is formed as by-product during the reaction, but acidity of the catalyst not affected and thereby the catalyst activity. The excess water present in the system could not affect the acidic sites, as it forms a binary mixture with acetic acid used as a solvent, apart from acting as an acylating agent in the present reaction. Indeed the metal-hydrated montmorillonite are more reactive, since the interlayer acidity increases with increasing ratio of charge to ionic radius of the cation. Moreover $La^{3+}$ has lower redox potential which can polarize the carboxylic acid more strongly. The sustained long lasting activity of the catalyst over number of the cycles is ascribed to the generation of Bronsted acid sites as described. Moreover the cationic-aqua complex located in the interlayers has been countered with an array of negative layer of charges that do not allow the cationic complex to go out of the interlayers. This is also attributed to the long lasting activity of the catalyst for number of cycles.

EXAMPLES

The following examples are given by way of illustration of the present invention and should not be construed to limit the scope of present disclosure. It is to be understood that both the foregoing general description and the following detailed description are exemplary and explanatory only and are intended to provide further explanation of the claimed subject matter.

Catalyst Preparation

Example 1

Lanthanum oxide supported montmorillonite ($La_2O_3$/Mont) (La=12 wt % with respect to catalyst composition, Atomic Absorption Spectroscopy, AAS analysis): About 200 mL of deionised water was taken into a 1 litre four neck round bottom flask and stirred at 25° C. with an overhead mechanical stirrer. 57.5456 g of lanthanum (III) trifluromethanesulfonate was added to deionised water and stirred to obtain a solution. 100 g of montmorillonite was added into the round bottom flask and the resulting slurry was aged at 65° C. for 12 hours. 150 g of solid product, was isolated by filtration, washed thoroughly with deionised water and dried at 110° C. for 12 h.

Example 2

Scandium oxide supported montmorillonite ($Sc_2O_3$/Mont) (Sc=12 wt % with respect to catalyst composition): About 200 ml of deionised water was taken into a 1 litre four necked round bottom flask and stirred at 25° C. with an overhead mechanical stirrer. 130.1649 g of scandium (III) trifluromethanesulfonate was added to deionised water and stirred to obtain a solution. 100 g of montmorillonite was added into the round bottom flask. The resulting slurry was aged at 65° C. for 12 hours. 225 g of solid product, was isolated by filtration, washed thoroughly with deionised water and dried at 110° C. for 12 h.

Example 3

Titanium oxide supported montmorillonite ($TiO_2$/Mont) (Ti=12 wt % wrt catalyst composition: About 200 ml of deionised water was taken into a 1 litre four necked round bottom flask and stirred at 25° C. with an overhead mechanical stirrer. 183.3782 g of titanium (IV) trifluromethanesulfonate was added to deionised water and stirred to obtain a solution. 100 g of montmorillonite was added into the round bottom flask. The resulting slurry was aged at 65° C. for 12 hours. 280 g of solid product was isolated by filtration, washed thoroughly with deionised water and dried at 110° C. for 12 h.

Example 4

Iron oxide supported montmorillonite ($Fe_2O_3$/Mont) (Fe=12 wt % wrt catalyst composition: About 200 ml of deionised water was taken into a 1 litre four necked round bottom flask and stirred at 25° C. with an overhead mechanical stirrer. 122.8253 g of Ferric (III) chloride was added to deionised water and stirred to obtain a solution. 100 g of montmorillonite was added into the round bottom flask. The resulting slurry was aged at 65° C. for 12 hours. 220 g of solid product was isolated by filtration, washed thoroughly with deionised water and dried at 110° C. for 12 h.

Example 5

Cerium oxide supported montmorillonite ($Ce_2O_3$/Mont) (Ce=12 wt % wrt catalyst composition: About 200 ml of deionised water was taken into a 1 litre four necked round bottom flask and stirred at 25° C. with an overhead mechanical stirrer. 57.1583 g of cerium (IV) trifluromethanesulfonate was added to deionised water and stirred to obtain a solution. 100 g of montmorillonite was added into the round bottom flask. The resulting slurry was aged at 65° C. for 12 hours. 155 g of solid product was isolated by filtration, washed thoroughly with deionised water and dried at 110° C. for 12 h.

Example 6

Ytterbium oxide supported montmorillonite ($Yb_2O_3$/Mont) (Yb=12 wt % wrt catalyst composition: About 200 ml of deionised water was taken into a 1 litre four necked round bottom flask and stirred at 25° C. with an overhead mechanical stirrer. 48.8787 g of ytterbium (III) trifluromethanesulfonate was added to deionised water and stirred to obtain a solution. 100 g of montmorillonite was added into the round bottom flask. The resulting slurry was aged at 65° C. for 12 hours. 145 g of solid product was isolated by filtration, washed thoroughly with deionised water and dried at 110° C. for 12 h.

Example 7

5.55 g of La(III) trifluromethane sulfonate was dissolved in 100 mL deionised water. To this solution, 25 g of montmorillonite was added and stirred at 65° C. for 12 hours. The solid product (31 g), was isolated by filtration, washed thoroughly with deionised water and dried at 110° C. for 12 h. The percentage of the metal loaded on the support was estimated by atomic absorption spectroscopy and was about 5 wt %.

Example 8

11.73 g of La(III) trifluromethane sulfonate was dissolved in 100 mL deionised water. To this solution 25 g of montmorillonite was added and stirred at 65° C. for 12 hours. The solid product (37 g), was isolated by filtration, washed thoroughly with deionised water and dried at 110° C. for 12 h. The percentage of the metal loaded on the support was estimated by atomic absorption spectroscopy and was about 10 wt %.

Example 9

18.62 g of La(III) trifluromethane sulfonate was dissolved in 100 mL deionised water. To this solution 25 g of montmorillonite was added and stirred at 65° C. for 12 hours. The solid product (44 g), was isolated by filtration, washed thoroughly with deionised water and dried at 110° C. for 12 h. The percentage of the metal loaded on the support was estimated by atomic absorption spectroscopy and was about 15 wt %.

Example 10

23.46 g of La(III) trifluromethane sulfonate was dissolved in 100 mL deionised water. To this solution 25 g of montmorillonite was added and stirred at 65° C. for 12 hours. The solid product (49 g), was isolated by filtration, washed thoroughly with deionised water and dried at 110° C. for 12 h. The percentage of the metal loaded on the support was estimated by atomic absorption spectroscopy was about 20 wt %.

Procedure for Acylation of Crude Glycerol Using Aliphatic Open Chain Linear Acetic Acid

Example 11

In a 600 mL parr reactor flask, crude glycerol (100 ml, 1.0 equiv), linear aliphatic acid, acetic acid (200 mmol, 3 equiv), 0.25 g of catalyst composition as described in examples 1-10 were taken and the mixture was stirred at temperature 110° C. for 2.5 h under closed condition. The progress of the reaction was monitored by HPLC and on completion of the reaction (2.5 h), the reaction mixture was centrifuged to separate the catalyst. The solid residue was washed several times with methanol to make the catalyst free from organic matter; the centrifugate was then washed with water and dried over anhyd. $Na_2SO_4$, the reaction mixture was concentrated under reduced pressure to give the crude product. The product was analyzed by high performance liquid chromatography to detect monoacetyl glycerol (MAG, 1%), diacetylglycerol (DAG, 2%) and triacetyl glycerol (TAG, 97%) for 100% conversion of glycerol.

Compounds were identified by HPLC and the conditions as follows:

Injection: 20 µl, Mobile phase: Ultra pure water

Flow rate: 0.8 ml/min

Analytical column: Suplecogel CA column

Dimensions: 30 cm×7.8 mm ID

Detector: RID, Column Temp.: 80° C.

The specification of crude glycerine obtained from biodiesel production and used for the preparation of ester of glycerol is provided in Table 1.

TABLE 1

Specification of crude glycerine

| Property | Value | Unit |
| --- | --- | --- |
| Genetically modified origin | possible | |
| Glycerol content | 77-90% | wt % A.R |
| Ash content | 3.5-7% | wt % A.R |
| Moisture content | 0.1-13.5% | wt % A.R |
| Lower calorific value | 14.9-17.5 | Wt % A.R |
| Kinematic viscosity | 120 | mg/kg A.R |
| 3-Monopropylenediol | 200-13,500 | $Mm^2$/s |
| Methanol | 0.01-3% | ppm |
| MONG* | 1.6-7.5% | wt % |
| pH | 4.5-7.4 | wt % |
| Sulphate | 0.01-1.04 | |
| Phosphate | 0.02-1.45 | wt % |
| Acetate | 0.01-6.0 | wt % |
| Na | 0.4-20 | g/kg |
| K | 0.03-40 | g/kg |
| Ca | 0.1-65 | mg/kg |
| Mg | 0.02-55 | mg/kg |
| Fe | 0.1-30 | mg/kg |
| Mn | <0.5 | mg/kg |

MONG* = Matter Organic Non Glycerol

Product Profile of the Process of Conversion of Crude Glycerol to Esters of Glycerol

Example 12

The product profile of the reaction of crude glycerol in presence of acetic acid and catalyst composition described above are provided in Table 2.

TABLE 2

Conversion and yield

| Catalyst Composition (Examples) | Metal wt % on support | Reaction Time (h) | Conversion(%) | Yield (%) MAG | DAG | TAG |
|---|---|---|---|---|---|---|
| 2 | 12 | 5 | 30 | 25 | 5 | 0 |
| 3 | 12 | 5 | 15 | 15 | 0 | 0 |
| 4 | 12 | 5 | 2 | 2 | 0 | 0 |
| 5 | 12 | 5 | 70 | 10 | 15 | 45 |
| 6 | 12 | 5 | 55 | 18 | 32 | 5 |
| 7 | 5 | 20 | No conversion of glycerol observed | 0 | 0 | 0 |
| 8 | 10 | 15 | 60 | 40 | 20 | 0 |
| 1 | 12 | 5 | 98 | 0 | 1 | 97 |
| 9 | 15 | 5 | 99 | 2 | 15 | 82 |
| 10 | 20 | 5 | 97 | 15 | 35 | 47 |

Table 2 depicts the catalytic performance of the catalyst composition. It can be inferred that the catalytic performance of the catalytic composition varied significantly with ionic radius. The catalyst composition including the transitional metal cation having the largest ionic radii, i.e., La$^{3+}$ afforded TAG with the highest selectivity and conversion, while the use of smaller cations in the catalyst composition such as Sc, Yb, and Ce gave less satisfactory results in terms of selectivity. Without being bound by theory, the superior activity in terms of selectivity attained with transitional metals with larger ionic radii might be attributed to increased coordination numbers, where the binding of substrates to metals would be allowed to access a reasonable transition state even on the solid surface. In contrast, the decrease in ionic radii severely limits the interaction of the substrate with metal because of decrease in number of available vacant coordination sites and hence decreases in selectivity. Further, it is surprisingly found that the catalyst composition containing 12 wt % lanthanum is able to effectively convert crude glycerol to TAG and DAG, with TAG as the major component.

Advantages Gained in the Example Illustrative Process in this Subject Matter:

The above mentioned implementation examples as described on this subject matter and its equivalent thereof have many advantages, including those which are described below:

The present disclosure comprises highly selective, efficient and recyclable catalyst system composed of La$_2$O$_3$/montmorillonite for the preparation of acetyl glycerols from chide glycerol with acetic acid at (110° C.) in 2-5 h. The product yield obtained in most of the cases are in the range of 90-99% in isolated form without any operational difficulty experienced during the course of the reaction.

The present process envisages the use of cheap and easily accessible crude glycerol and acetic acid as acylating agents for acylation of crude glycerol at mild temperature for the first time.

La$_2$O$_3$/montmorillonite, catalyst system used for acylation of crude glycerol is recyclable and reusable for at least next five consecutive cycles without loss of catalytic activity.

The present process envisages optimal use of La$_2$O$_3$/montmorillonite, to ensure highest conversion and selectivity.

An eco-friendly and very simple synthetic protocol is developed using cheap and non-corrosive La$_2$O$_3$/montmorillonite, catalyst system.

The reaction conditions are extremely mild. The selectivity, yield and purity of O-acylated products in the disclosed process are quite high.

Monitoring of the reaction and subsequent work-up procedures are easy.

The overall process is economical, the catalyst used is inert, eco-friendly and non-toxic. The catalyst used is immiscible and stable in organic as well as in aqueous phase. There is absolutely no leaching of the metal content during the reaction as well as during the workup.

Although the subject matter has been described in considerable detail with reference to certain examples and implementations thereof, other implementations are possible. As such, the spirit and scope of the appended claims should not be limited to the description of the preferred examples and implementations contained therein.

We claim:

1. A catalyst composition for producing ester(s) of glycerol comprising:
   a base catalyst comprising at least one selected from the group consisting of oxides of transitional metals, the base catalyst being in an amount in the range of 6% to 20% w/w of the total weight of the catalyst composition; and
   a support material, the support material being in an amount in the range of 80% to 94% w/w of the total weight of the catalyst composition,
   wherein the support material is based on phyllosilicates of montmorillonite structure, with a total surface area of 220 m$^2$/g to 300 m$^2$/g,
   the catalyst composition has a conversion rate of glycerol to glycerol ester of at least 55% at a reaction time of 5 hours to 15 hours and a temperature of 100° C. to 180° C., and
   the transitional metals comprise at least one selected from the group consisting of La, Pr, Nd, Pm, Sm, Eu, Gd, Tb, Dy, Ho, Er, Tm, and Yb.

2. The catalyst composition as claimed in claim 1, wherein the base catalyst is in cationic form.

3. The catalyst composition as claimed in claim 1, wherein the support material is acid treated.

4. The catalyst composition as claimed in claim 1, wherein the base catalyst further includes at least one oxide selected from the group consisting of scandium oxide (Sc$_2$O$_3$), titanium oxide (Ti$_2$O$_3$), iron oxide (Fe$_2$O$_3$), and combinations thereof.

5. The catalyst composition as claimed in claim 1, wherein the base catalyst is in an amount in the range of 6 to 18% w/w of the total weight of the catalyst composition.

6. The catalyst composition as claimed in claim 1, wherein the catalyst composition is used for preparation of mono-, di- and triesters of glycerol, and combinations thereof.

7. The catalyst composition of claim 1, wherein the base catalyst further includes at least a salt of a transitional metal selected from the group consisting of scandium (Sc), titanium (Ti), and iron (Fe).

8. The catalyst composition of claim 7, wherein the salt of the transitional metal includes scandium (III) trifluoromethanesulfonate (C$_4$F$_{12}$O$_{12}$S$_4$Sc), scandium (III) chloride hexahydrate (ScCl$_3$.6H$_2$O), scandium (III) hydroxide (Sc(OH)$_3$), scandium (III) nitrate hydrate (Sc(NO$_3$)$_3$.xH$_2$O), scandium (III) oxalate pentahydrate (Sc$_2$(C$_2$O$_4$)$_3$.10H$_2$O), or scandium (III) sulfate pentahydrate (Sc$_2$(SO$_4$)$_3$.5H$_2$O), or a combination thereof.

9. The catalyst composition of claim 7, wherein the salt of the transitional metal includes titanium (IV) trifluoromethanesulfonate ($C_4F_{12}O_{12}S_4Ti$), titanium (IV) chloride ($TiCl_4$), titanium (IV) nitrate ($Ti(NO_3)_4$), titanium (III) oxalate decahydrate ($Ti_2(C_2O_4)_3 \cdot 10H_2O$), or titanium (IV) sulfate ($Ti(SO_4)_2$), or a combination thereof.

10. The catalyst composition of claim 7, wherein the salt of the transitional metal includes iron (III) trifluromethanesulfonate ($C_3F_9FeO_9S_3$), iron (III) hydroxide ($Fe(OH)_3$), iron (III) nitrate nonahydrate ($Fe(NO_3)_3 \cdot 9H_2O$), iron(III) oxalate hexahydrate ($Fe(C_2O_4)_3 \cdot 6H_2O$), or iron (III) sulfate ($Fe_2(SO_4)_3$), or a combination thereof.

11. The catalyst composition of claim 1, wherein the base catalyst comprises oxide of La, in an amount such that the La is in the range of 10 to 20% w/w of the total weight of the catalyst composition, and the catalyst composition has a conversion rate of glycerol to triacetylglycerol ester of 97% at a reaction time of 5 hours and a temperature of 110°.

12. The catalyst composition of claim 1, wherein the oxide of La of the base catalyst is in an amount such that the amount of La in the range of 12 to 20% w/w of the total weight of the catalyst composition.

13. The catalyst composition of claim 1, wherein the oxide of Yb of the base catalyst is in an amount such that the amount of Yb is 12% w/w of the total weight of the catalyst composition.

14. The catalyst composition of claim 1, wherein the base catalyst comprises an oxide of Pr, Nd, Pm, Sm, Eu, Gd, Tb, Dy, Ho, Er, or Tm.

15. The catalyst composition of claim 1, wherein the catalyst composition is in a dried condition and is dried at 110° C. for 12 h.

16. The catalyst composition as claimed in claim 1, wherein the support material is treated with acetic acid.

17. A process for producing a mixture of mono-, di- and triesters of glycerol, the process comprising:

contacting a catalyst composition with a compound in the presence of an optional polar solvent at a temperature in the range of 100 to 180° C. for a period of 2 to 5 hours,

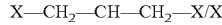

wherein the catalyst composition comprises:
a base catalyst comprising at least one selected from the group consisting of oxides of transitional metals, the base catalyst being in an amount in the range of 6 to 20% w/w of the total weight of the catalyst composition; and a support material, the support material being in an amount in the range of 80 to 94% w/w of the total weight of the catalyst composition, wherein the support material is based on phyllosilicates of montmorillonite structure with a total surface area of 220 to 300 $m^2/g$, the catalyst composition has a conversion rate of glycerol to glycerol ester of at least 55% at a reaction time of 5-15 hours and a temperature of 100 to 180° C., and the transitional metals comprise at least one selected from the group consisting of La, Pr, Nd, Pm, Sm, Eu, Gd, Tb, Dy, Ho, Er, Tm, and Yb, the compound is represented by the following general formula I:

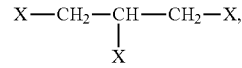

wherein 1-3 of X groups of the general formula I are OH or 0-2 of X groups of the general formula I are —OC(O)R1, where R1 is —$(CH_2)_n$—$CH_3$, and where n is 0 to 30, all R1 groups are identical or different in the presence of HOC(O)R2, where R2 is —$(CH_2)_n$—$CH_3$, and where n is 0 to 30; and isolating glycerol esters, the glycerol esters having a general formula II:

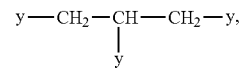

wherein 0-2 of Y groups are OH or 1-3 of Y groups are —OC(O)R3, where R3 is —$(CH_2)_n$—$CH_3$, and where n is 0 to 30, and all R3 groups are identical or different.

18. The process as claimed in claim 17, wherein 3 of X groups of the general formula I are OH.

19. The process as claimed in claim 17, wherein R2 of HOC(O)R2 is —$(CH_2)_n$—$CH_3$, wherein n is 0-20.

20. The process as claimed in claim 17, wherein R3 is —$(CH_2)_n$—$CH_3$, wherein n is 0-20.

* * * * *